US00PP27141P3

(12) United States Plant Patent
Mehlenbacher et al.

(10) Patent No.: US PP27,141 P3
(45) Date of Patent: Sep. 13, 2016

(54) ***CORYLUS* PLANT NAMED 'WEPSTER'**

(50) Latin Name: *Corylus avellana*
Varietal Denomination: Wepster

(71) Applicants: Shawn A. Mehlenbacher, Corvallis, OR (US); David C. Smith, Corvallis, OR (US); Rebecca L. McCluskey, Corvallis, OR (US)

(72) Inventors: Shawn A. Mehlenbacher, Corvallis, OR (US); David C. Smith, Corvallis, OR (US); Rebecca L. McCluskey, Corvallis, OR (US)

(73) Assignee: State of Oregon Acting by and through the State Board of Higher Education on behalf of Oregon State University, Corvallis, OR (US)

( * ) Notice: Subject to any disclaimer, the term of this patent is extended or adjusted under 35 U.S.C. 154(b) by 332 days.

(21) Appl. No.: 13/998,648

(22) Filed: Nov. 19, 2013

(65) Prior Publication Data

US 2015/0143594 P1 May 21, 2015

(51) Int. Cl.
*A01H 5/08* (2006.01)

(52) U.S. Cl.
USPC ..... Plt./152

(58) Field of Classification Search
USPC ..... Plt./152, 216
See application file for complete search history.

(56) References Cited

PUBLICATIONS

Bassil et al, "Additional Microsatellite Markers of the European Hazelnut," *Acta Hortic.* 686:105-110, 2005.
Bassil et al, "Microsatellite Markers in Hazelnut: Isolation, Characterization, and Cross-species Amplification," *J. Amer. Soc. Hort. Sci.*, 130(4):543-549, 2005.
Bassil et al, "Nuclear and chloroplast microsatellite markers to assess genetic diversity and evolution in hazelnut species, hybrids and cultivars," *Genet. Resour. Crop Evol.*, 60(2):543-568, 2012.
Boccacci et al, "Characterization and evaluation of microsatellite loci in European hazelnut (*Corylus avellana* L.) and their transferability to other *Corylus* species," *Molecular Ecology Notes*, 5:934-937, 2005.
Boccacci et al, "DNA typing and genetic relations among European hazelnut (*Corylus avellana* L.) cultivars using microsatellite markers," *Genome*, 49:598-611, 2006.
Gökirmak et al, "Characterization of European hazelnut (*Corylus avellana*) cultivars using SSR markers," *Genet. Resour. Crop Evol.*, vol. 56(2), pp. 147-172, 2008.
Gürcan et al, "Genetic diversity in hazelnut (*Corylus avellana* L.) cultivars from Black Sea countries assessed using SSR markers," *Plant Breeding*, 129:422-434, 2010.
Gürcan et al, "Development, characterization, segregation, and mapping of microsatellite markers for European hazelnut (*Corylus avellana* L.) from enriched genomic libraries and usefulness in genetic diversity studies," *Tree Genetics & Genomes*, 6:513-531, 2010.
Gürcan et al, "Transferability of Microsatellite Markers in the Betulaceae," *J. Amer. Soc. Hort. Sci.* 135(2):159-173, 2010.
Gürcan and Mehlenbacher. "Development of microsatellite marker loci for European hazelnut (*Corylus avellana* L.) from ISSR fragments," *Molecular Breeding* 26:551-559, 2010.
Mehlenbacher et al., "Inheritance of the Cutleaf Trait in Hazelnut," *HortScience*, 30(3):611-612, 1995.
Mehlenbacher et al., "'Tonda Pacifica' hazelnut," *HortScience* 46:505-508, 2011.
Mehlenbacher et al., "'Santiam' hazelnut," *HortScience* 42:715-717, 2007.
Mehlenbacher et al., "RAPD markers linked to eastern filbert blight resistance in *Corylus avellana," Theor. Appl. Genet.*, 108:651-656, 2004.
Sathuvalli et al., "Characterization of American hazelnut (*Corylus americana*) accessions and *Corylus americana*×*Corylus avellana* hybrids using microsatellite markers," *Genet. Resour. Crop. Evol.*, 59:1055-1075, 2012.

*Primary Examiner* — Susan McCormick Ewoldt
*Assistant Examiner* — Karen Redden
(74) *Attorney, Agent, or Firm* — Klarquist Sparkman, LLP

(57) ABSTRACT

A new and distinct cultivar of *Corylus* plant named 'Wepster' characterized by high vigor and an upright-spreading plant habit, yellowish-green developing and fully expanded leaves during the spring and summer, resistance to eastern filbert blight caused by the fungus *Anisogramma anomala* (Peck) E. Müller, presence of random amplified polymorphic DNA markers 152-800 and 268-580 amplified by the polymerase chain reaction and which are linked to a dominant allele for resistance to eastern filbert blight from the cultivar Gasaway, expression of incompatibility alleles $S_1$ and $S_2$ in the styles, and DNA fingerprints at 8 of 20 microsatellite marker loci differ from both parents OSU 440.005 and 'Tonda Pacifica', and from one parent at an additional 12 marker loci.

7 Drawing Sheets

ACKNOWLEDGMENT OF GOVERNMENT SUPPORT

This invention was made with government support under Specific Cooperative Agreement No. 58-5358-9-447 awarded by the United States Department of Agriculture. The government has certain rights in the invention.

Botanical denomination: *Corylus avellana.*
Variety designation: 'Wepster'.

BACKGROUND

The present Invention relates to a new and distinct cultivar of *Corylus* plant, botanically known as *Corylus avellana*, and hereinafter referred to by the name 'Wepster'. *Corylus avellana* is in the family Betulaceae.

The new *Corylus* resulted from a controlled cross of female parent 'Tonda Pacifica' and male parent OSU 440.005 (unpatented) made in 1997 by Shawn A. Mehlenbacher and David C. Smith. 'Tonda Pacifica' is protected by U.S. Plant Pat. No. 22,715 (issued May 8, 2012). Hybrid seeds from the cross were harvested in August 1997, stratified, and seedlings grown in the greenhouse during the summer of 1998. From this cross, a total of 182 seedling trees were planted in the field in Corvallis, Oreg., USA in October, 1998. 'Wepster' was discovered and selected by the Inventors as a single plant within the progeny of the stated cross-pollination in a controlled environment in Corvallis, Oreg. It was originally assigned the designation OSU 894.030 (unpatented), which indicates the row and tree location of the original seedling. OSU 440.005 (unpatented) is from a cross of OSU 49.073× VR 8-32 (both unpatented). OSU 49.073 is from a cross of OSU 14.084×'Tombul Ghiaghli' (both unpatented). OSU 14.084 is from a cross of 'Barcelona'×'Daviana' (both unpatented). VR 8-32 is from a cross of 'Montebello'×'Gasaway' (both unpatented). 'Tonda Gentile delle Langhe' (unpatented), the female parent of 'Tonda Pacifica', is an important cultivar in Piemonte, northern Italy. 'Barcelona', Oregon's most widely planted hazelnut cultivar, is known as 'Castanyera' (unpatented) where it originated in Catalunya, Spain. 'Daviana', originally from England, is the most widely planted pollinizer in 'Barcelona' orchards. 'Tombul Ghiaghli', obtained from Greece, is similar to the Turkish cultivar 'Mincane' (unpatented). 'Montebello' is widely grown under several names in Sicily. 'Gasaway' is the source of a single dominant gene for resistance to eastern filbert blight.

The new cultivar was asexually reproduced by rooted suckers annually for eight years (2004-05 and 2007-12) in Corvallis, Oreg. The new cultivar was also asexually propagated by whip grafting in 2005 in Corvallis, Oreg. The unique features of this new *Corylus* are stable and reproduced true-to-type in successive generations of asexual reproduction.

SUMMARY

The following traits have been repeatedly observed and are determined to be the unique characteristics of 'Wepster'. These characteristics in combination distinguish 'Wepster' as a new and distinct cultivar:

1. High vigor and upright-spreading plant habit.
2. Yellowish-green developing and fully expanded leaves during the spring and summer.
3. Resistance to eastern filbert blight caused by the fungus *Anisogramma anomala* (Peck) E. Müller.
4. Presence of random amplified polymorphic DNA markers 152-800 and 268-580 in DNA of 'Wepster' amplified by the polymerase chain reaction. These two markers are linked to a dominant allele for resistance to eastern filbert blight from the cultivar Gasaway (unpatented).
5. Expression of incompatibility alleles $S_1$ and $S_2$ in the styles.
6. DNA fingerprints at 8 of 20 microsatellite marker loci differ from both parents, 'Tonda Pacifica' and OSU 440.005, and from one parent at an additional 12 marker loci. Additional DNA fingerprints of grandparent 'Tonda Gentile delle Langhe', standard cultivar 'Barcelona', eastern filbert blight resistance source 'Gasaway' and five cultivars released by Oregon State University hazelnut breeding program are shown in attached Table 2.

In comparisons in two replicated trials conducted in Corvallis, Oreg., plants of the new *Corylus* differed from plants of the *Corylus avellana* cultivar 'Barcelona' (unpatented), and other cultivars and selections of *Corylus avellana* known to the Inventors primarily in nut size, nut shape, kernel percentage (ratio of kernel weight to nut weight), frequency of blank nuts (nuts lacking kernels), time of pollen shed, time of nut maturity, length of the husk or involucre, and plant size. For example:

- Blank nut frequency: 'Wepster' in two trials 7.25%, 'Barcelona' in one trial 7.7%;
- Pollen shed: 'Wepster' sheds pollen about 6 days later than 'Barcelona' (average of 3 years, 2011-13);
- Nut maturity: 'Wepster' nuts mature 8 days earlier than Barcelona; and
- Husk Length: 'Wepster' 2 times nut length, 'Barcelona' 1.5 times nut length.

BRIEF DESCRIPTION OF THE DRAWINGS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Corylus*.

DETAILED DESCRIPTION

Figure 1:
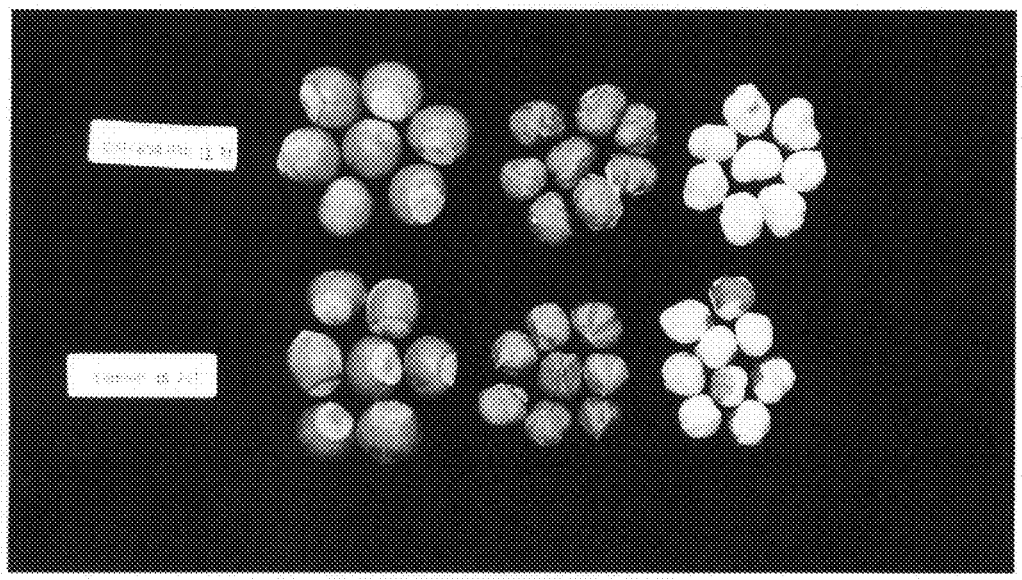
FIG. 1 shows typical nuts, raw kernels, and blanched kernels of 'Wepster' hazelnut (OSU 894.030) compared to those of 'Yamhill' hazelnut.
Figure 2:
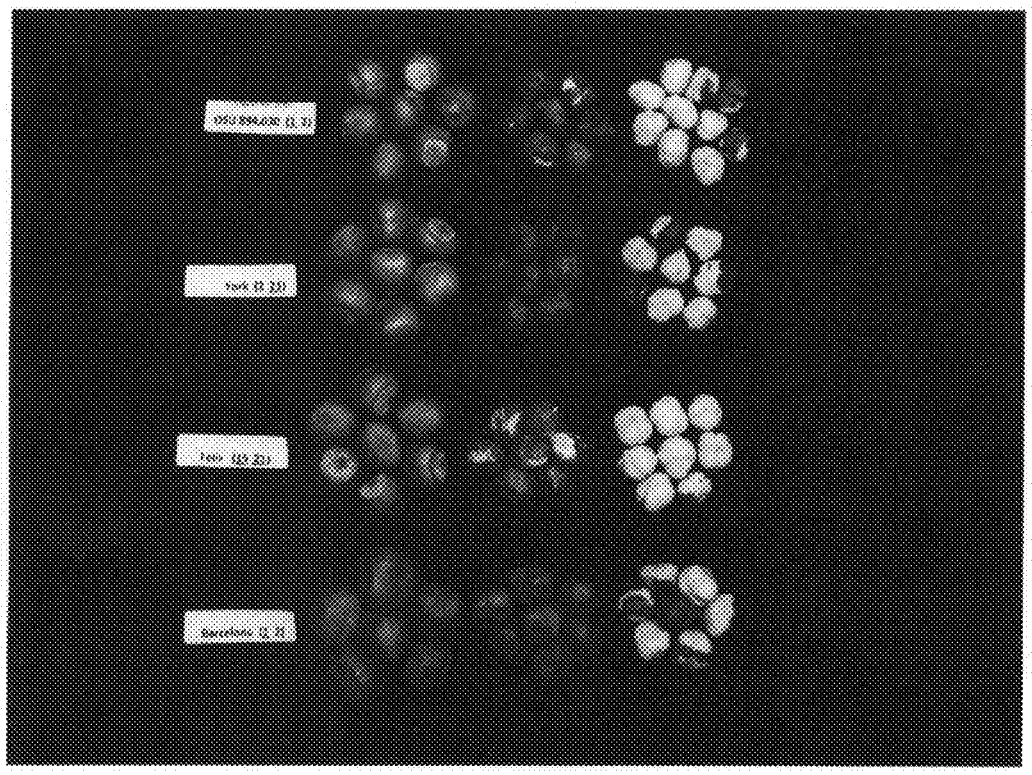
FIG. 2 shows the typical nuts, raw kernels, and blanched kernels of 'Wepster' hazelnut (OSU 894.030) compared to those of 'Barcelona', 'Felix,' and 'York' hazelnut cultivars.
Figure 3:
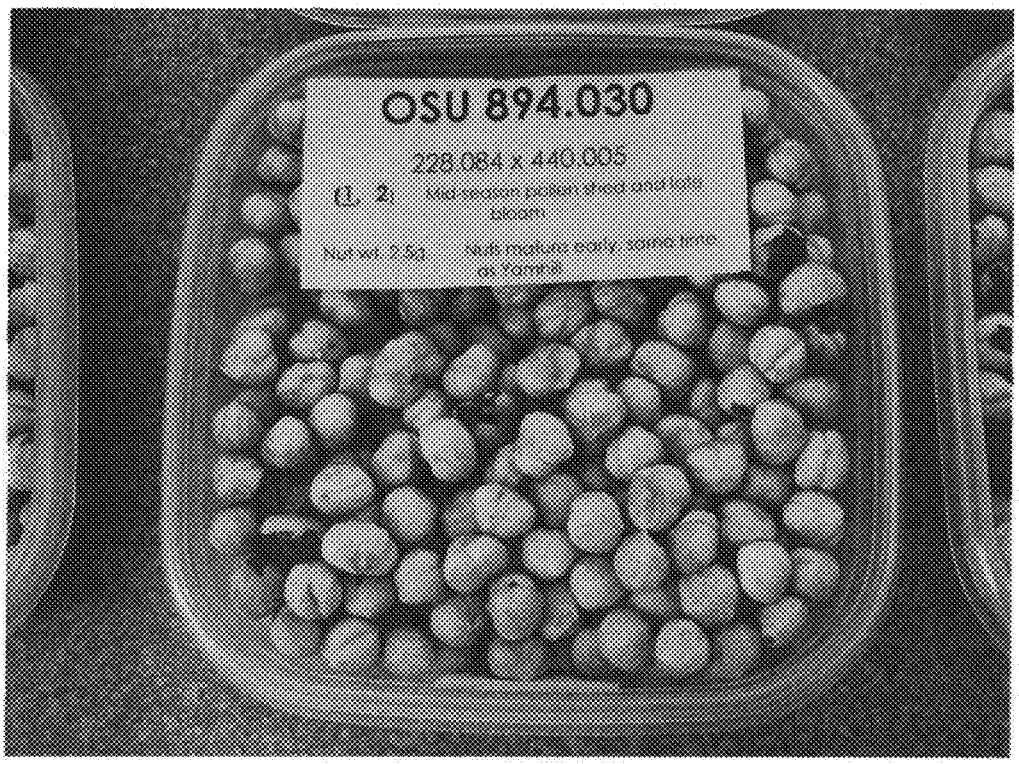
FIG. 3 shows the blanched kernels of 'Wepster' hazelnut (OSU 894.030).
Figure 4:
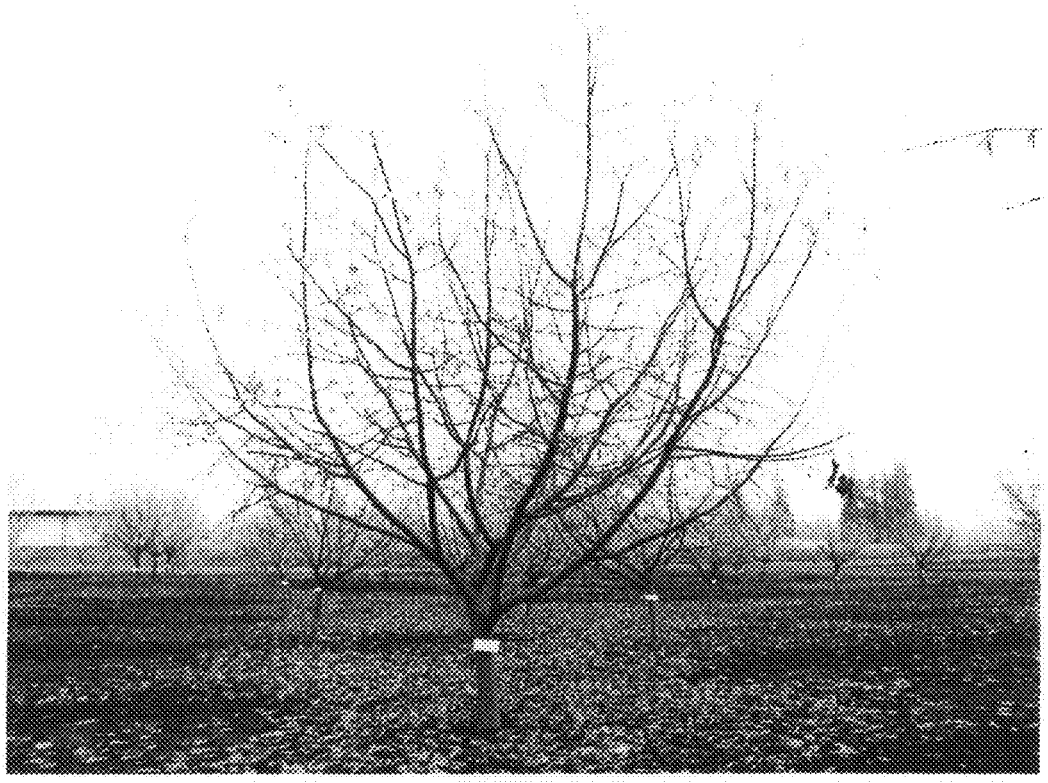
FIG. 4 shows the tree of the new cultivar 'Wepster' growing in a field in January, in Corvallis, Oreg.
Figure 5:
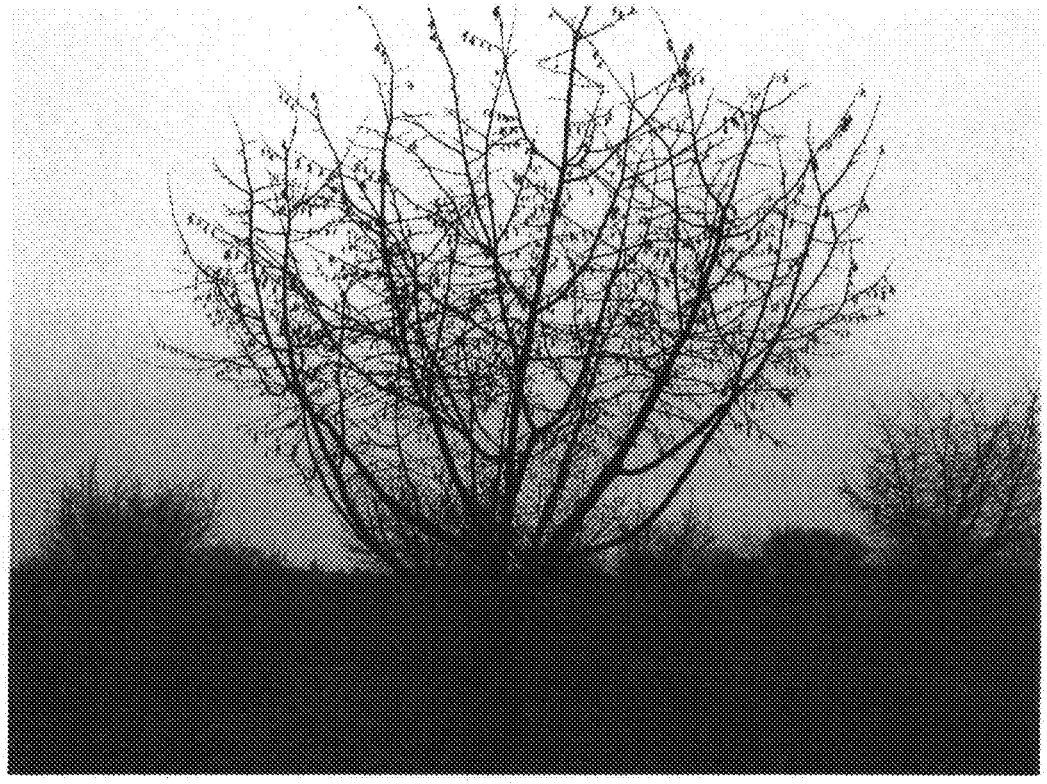
FIG. 5 shows a pruned tree of the new cultivar 'Wepster' in January, in Corvallis, Oreg.
Figure 6:
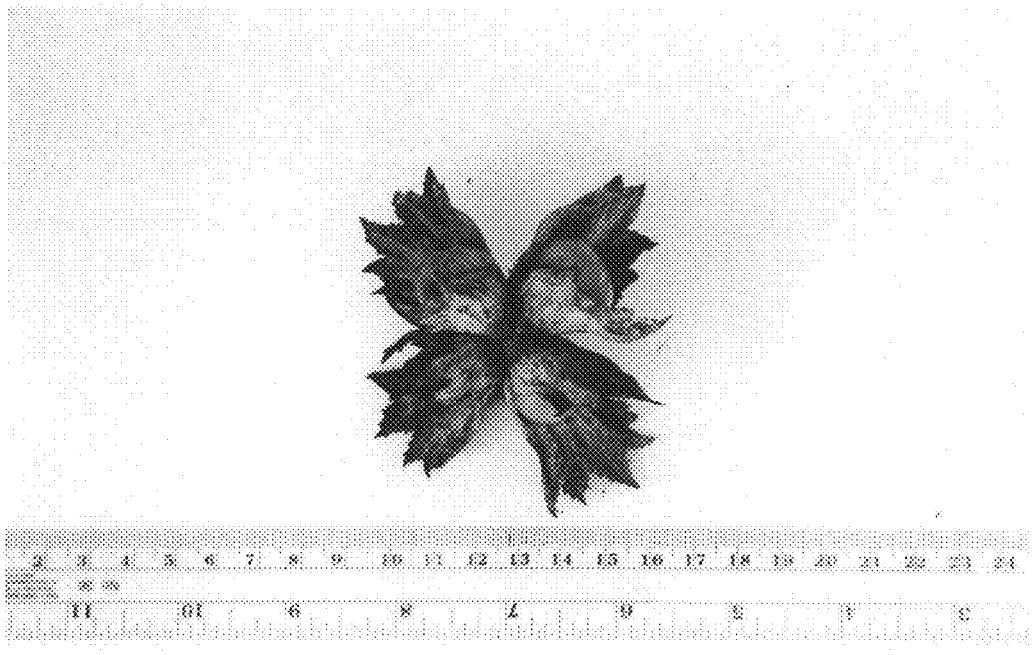
FIG. 6 shows the husks and nuts of 'Wepster' hazelnut.
Figure 7:
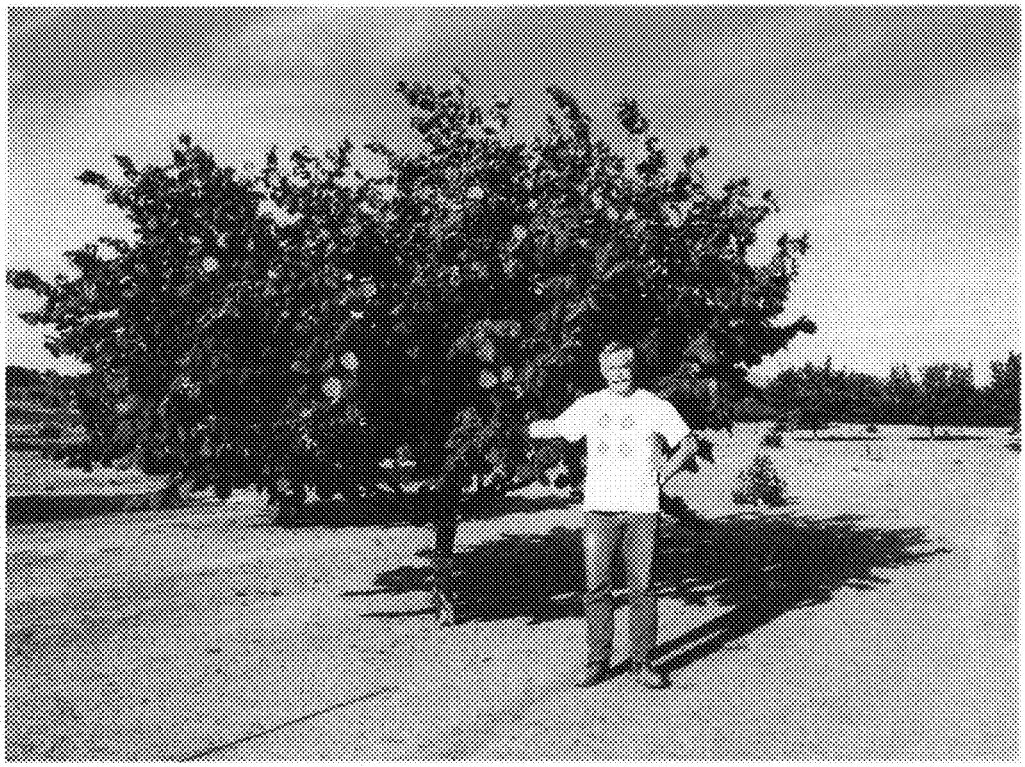
FIG. 7 shows a tree of the new cultivar 'Wepster,' $8^{th}$ leaf, growing in a field in the summer, in Corvallis, Oreg.

The cultivar 'Wepster' has not been observed under all possible environmental conditions. The phenotype may vary somewhat with variations in environment such as temperature and light intensity, without, however, any variance in genotype. The aforementioned images and following observations and measurements describe plants grown in Corvallis, Oreg. under commercial practice outdoors in the field during the fall, winter and spring. Plants used for the photographs and description were propagated by tie-off layerage and growing on their own roots, and about seven years old. In the following description, color references are made to *The Royal Horticultural Society Colour Chart,* 1966 Edition, except where general terms of ordinary dictionary significance are used. The list of UPOV descriptors are from the Mar. 28, 1979 Hazelnut guidelines from UPOV.

Botanical classification: *Corylus avellana* cultivar Wepster.

Parentage:

*Female, or seed, parent.—Corylus avellana* cultivar Tonda Pacifica (U.S. Plant Pat. No. 22,715).

*Male, or pollen, parent.—Corylus avellana* selection OSU 440.005 (unpatented).

Propagation (type rooted suckers):

*Time to initiate roots*.—About 30 days at 20° C.

*Time to produce a rooted young plant*.—About six months at 22° C.

*Root description*.—Fine to thick; freely branching; creamy white in color.

Propagation (type whip grafting):

*Time to budbreak on the scions*.—About 14 days at 25° C.

*Time to produce a grafted plant*.—About six months at 25° C.

Plant description:

*Type*.—Natural habit is a perennial shrub, but in commercial orchards is a single-trunk tree. Upright-spreading plant habit.

*Growth and branching habit*.—Freely branching; about 15 lateral branches develop per plant. Pinching, i.e., removal of the terminal apices, enhances branching with lateral branches potentially forming at every node.

*Size*.—Plant height. — About 6 meters; plant diameter or spread is about 6 meters.

*Vigor*.—High vigor growth habit.

Lateral branch description:

*Length*.—About 32 cm.

*Diameter*.—About 6 mm.

*Internode length*.—About 3.0 cm.

*Texture*.—Smooth, glabrous.

*Strength*.—Strong.

*Color*.—Immature — 152B; mature — 152B.

Foliage description:

*Arrangement*.—Alternate, simple.

*Length*.—About 10.2 cm.

*Width*.—About 9.1 cm.

*Shape*.—Oblong to ovate.

*Apex*.—Obtuse to acute.

*Base*.—Cordate.

*Margin*.—Serrate.

*Texture, upper and lower surfaces*.—Slightly pubescent.

*Venation pattern*.—Pinnate.

*Leaf bud shape*.—Globular.

*Time of leaf budbreak*.—Descriptor=6 (medium to late).

*Coloration of leaf bud*.—178C.

*Time of leaf fall*.—Descriptor=4 (between 'Tonda Gentile delle Langhe' and 'Barcelona').

*Color*.—Developing foliage, upper surface 144A, lower surfaces: 187A. Fully expanded foliage, upper surface: Spring and summer, 143A; late summer and fall, 143A. Fully expanded foliage, lower surface: Spring and summer, 139C; late summer and fall, 139C. Venation, upper surface: Spring and summer, 139C; late summer and fall, 139C. Venation, lower surface: Spring and summer, 139D; late summer and fall, 139D.

Petiole description:

*Length*.—About 2.7 cm.

*Diameter*.—About 1.8 mm.

*Texture, upper and lower surfaces*.—Pubescent.

*Color*.—Upper surface: Spring and summer, 139D; late summer and fall, 139D. Lower surface: Spring and summer, 139D; late summer and fall, 139D.

Flower description:

*Male inflorescences*.—Catkins, color prior to elongation 176C.

*Female inflorescence*.—Style color 048B to 047B.

*Time of pollen shed*.—Descriptor=6 (same as 'Daviana', 'Cosford', and 'Tonda Romana').

*Catkin length*.—29.5 mm, descriptor=5 (medium).

*Time of female flowering*.—Descriptor=5 (medium).

*Time of female flowering compared to male flowering*.—Protogyny, descriptor=1 (earlier).

*Involucre constriction*.—Absent.

*Involucre length*.—Twice length of nut, descriptor=7.

*Size of indentation*.—Descriptor=7 (strong).

*Strength of serration of indentation*.—Descriptor=7 (strong).

*Pubescence on husk*.—Descriptor=9 (present).

*Thickness of callus at base*.—Descriptor=5 (medium).

*Jointing of bracts*.—Descriptor=2 (on one side).

Nut description:

*Length*.—About 18.3 mm.

*Width*.—About 19.0 mm.

*Depth*.—About 16.6 mm.

*Nut shape*.—Round.

*Nut shape index [(width+depth)/2*length]*—0.97.

*Nut compression index (width/depth)*.—1.15.

*Nut shell color*.—164A.

*Nut weight*.—About 2.39 grams.

*Kernel weight*.—About 1.11 grams.

*Kernel percentage (kernel weight/nut weight)*.—About 43.9%.

*Number of fruits per cluster*.—Two to three.

*Number of stripes on shell*.—Descriptor=5 (medium).

*Prominence of fruit apex*.—Slight, descriptor=3.

*Size of fruit pistil*.—Very small, descriptor=3.

*Hairiness of top of fruit*.—Weak, descriptor=3.

*Curvature of nut basal scar*.—Flat.

*Double kernels*.—Absent.

*Kernel shape*.—Globular.

*Shape of kernel in cross-section*.—Circular.

*Lateral groove in kernel*.—Absent.

*Corkiness of pellicle of kernel*.—Descriptor=5 (medium corky).

*Nut yield (pounds per tree or per acre)*.—Total 25.91 kg per tree, years 3 to 7 ($1^{st}$ trial) (very high) total 19.67 kg per tree, years 3 to 7 ($2^{nd}$ trial).

*Storability of fruits*.—Excellent, similar to OSU releases and check cultivars.

Disease/pest resistance: Plants of the new *Corylus* are highly resistant to eastern filbert blight caused by the fungus *Anisogramma anomala* (Peck) E. Müller. Plants of the new *Corylus* are highly resistant to bud mites (*Phytoptus avellanae* Nal.), while plants of 'Tonda Gentile delle Langhe' are highly susceptible, and plants of 'Barcelona' are highly resistant.

Temperature tolerance: Plants of the new *Corylus* have been observed to tolerate temperatures from −10 to 38 degrees C. in the field in Corvallis, Oreg.

TABLE 1

Primers and annealing temperatures for the 20 microsatellite marker loci used to fingerprint 'Wepster' and other hazelnut cultivars.

| Locus | Repeat motif | Size | $T_a$ | n | He | Ho |
|---|---|---|---|---|---|---|
| A614 | $(TC)_{17}(CA)_{10}$ NNN$(CA)_6$ | 125-156 | 60 | 14 | 0.85 | 0.85 |
| A616 | $(AC)_{11}$ | 136-162 | 60 | 13 | 0.85 | 0.85 |
| A640 | $(CT)_{15}(CA)_{13}$ | 354-378 | 67 | 11 | 0.80 | 0.73 |

TABLE 1-continued

Primers and annealing temperatures for the 20 microsatellite marker loci used to fingerprint 'Wepster' and other hazelnut cultivars.

| | | | | | | |
|---|---|---|---|---|---|---|
| B617 | $(GA)_{15}$ | 280-298 | 60 | 9 | 0.80 | 0.78 |
| B619 | $(TC)_{21}$ | 146-180 | 60 | 14 | 0.88 | 0.88 |
| B634 | $(AG)_{15}$ | 218-238 | 60 | 9 | 0.76 | 0.76 |
| B671 | $(AG)_6NN(GA)_{17}$ | 221-249 | 60 | 13 | 0.86 | 0.88 |
| B709 | $(GA)_{21}$ | 219-233 | 60 | 16 | 0.87 | 0.80 |
| B733 | $(TC)_{15}$ | 161-183 | 60 | 8 | 0.68 | 0.68 |
| B749 | $(TC)_{12}$ | 200-210 | 60 | 6 | 0.60 | 0.64 |
| B767 | $(TC)_{15}(AT)_7$ | 198-238 | 60 | 16 | 0.87 | 0.80 |
| B774 | $(AG)_{15}$ | 195-213 | 60 | 8 | 0.80 | 0.80 |
| B795 | $(TC)_8Ns(CT)_7Ns(CT)_{10}Ns(TC)_5$ | 296-332 | 60 | 12 | 0.76 | 0.74 |
| C115 | $(TAA)_5(GAA)_{12}$ | 167-226 | 60 | 14 | 0.80 | 0.80 |
| KG807 | $(TAAA)AA(TAAA)_2A(TAAA)_2$ | 226-248 | 54 | 4 | 0.67 | 0.78 |
| KG809 | $(AGG)_6$ | 333-345 | 55 | 5 | 0.66 | 0.64 |
| KG811 | $(GA)_{17}$ | 240-278 | 58 | 12 | 0.83 | 0.82 |
| KG827 | $(CT)_{13}AA(CA)_7$ | 264-282 | 67 | 9 | 0.78 | 0.84 |
| KG830 | $(CT)_{14}GTATT(CA)_8$ | 279-311 | 67 | 9 | 0.79 | 0.78 |
| Soman-G (=856-MS1-13) | $(AAT)_5$ | 193-200 | 54 | 3 | 0.60 | 0.98 |

| Locus | PIC | r | LG | Primers 5'-3' (forward) |
|---|---|---|---|---|
| A614 | 0.84 | 0.00 | 6 | Hex-TGGCAGAGCTTTGTCAGCTT (SEQ ID NO: 1) |
| A616 | 0.83 | 0.00 | 8 | Fam-CACTCATACCGCAAACTCCA (SEQ ID NO: 3) |
| A640 | 0.77 | 0.04 | 10 | F-TGCCTCTGCAGTTAGTCATCAAATGTAGG (SEQ ID NO: 5) |
| B617 | 0.78 | 0.01 | 8 | Fam-TCCGTGTTGAGTATGGACGA (SEQ ID NO: 7) |
| B619 | 0.87 | 0.00 | 3 | Fam-AGTCGGCTCCCCTTTTCTC (SEQ ID NO: 9) |
| B634 | 0.73 | 0.00 | 4 | Hex-CCTGCATCCAGGACTCATTA (SEQ ID NO: 11) |
| B671 | 0.84 | −0.01 | 9 | Hex-TTGCCAGTGCATACTCTGATG (SEQ ID NO: 13) |
| B709 | 0.86 | 0.04 | 8 | Fam-CCACCAACTGTTTCACACCA (SEQ ID NO: 15) |
| B733 | 0.63 | 0.00 | 7,2 | Ned-CACCCTCTTCACCACCTCAT (SEQ ID NO: 17) |
| B749 | 0.51 | −0.03 | 1 | Hex-GGCTGACAACACAGCAGAAA (SEQ ID NO: 19) |
| B767 | 0.86 | 0.04 | 8 | Fam-CCACCAACTGTTTCACACCA (SEQ ID NO: 21) |
| B774 | 0.77 | 0.01 | 5 | Ned-GTTTTGCGAGCTCATTGTCA (SEQ ID NO: 23) |
| B795 | 0.74 | 0.01 | NA | Fam-GACCCACAAACAATAACCTATCTC (SEQ ID NO: 25) |
| C115 | 0.77 | 0.00 | 4 | Fam-ATTTTCCGCAGATAATACAGG (SEQ ID NO: 27) |
| KG807 | 0.60 | −0.07 | 11 | AAGCAAGAAAGGGATGGT (SEQ ID NO: 29) |
| KG809 | 0.60 | 0.01 | 4 | Hex-AGGCATCAGTTCATCCAA (SEQ ID NO: 31) |
| KG811 | 0.81 | 0.01 | 2 | Ned-AAGGCGGCACTCGCTCAC (SEQ ID NO: 33) |
| KG827 | 0.75 | −0.04 | 9 | Fam-AGAACTCCGACTAATAATCCTAACCCTTGC (SEQ ID NO: 35) |
| KG830 | 0.76 | 0.00 | 9 | Ned-TGGAGGAAGTTTTGAATGGTAGTAGAGGA (SEQ ID NO: 37) |
| Soman-G (=856-MS1-13) | 0.51 | −0.27 | NA | Hex-TGGCGTTGCAACATATTCTC (SEQ ID NO: 39) |

TABLE 1-continued

Primers and annealing temperatures for the 20 microsatellite marker loci used to fingerprint 'Wepster' and other hazelnut cultivars.

| Locus | Primers 5'-3' (reverse) | Reference |
|---|---|---|
| A614 | R-GCAGTGGAGGATTGCTGACT (SEQ ID NO: 2) | Gurcan et al. 2010 |
| A616 | R-ATGGCTTTTGCTTCGTTTTG (SEQ ID NO: 4) | Gurcan et al. 2010 |
| A640 | Fam-CGCCATATAATTGGATGCTTGTTG (SEQ ID NO: 6) | Gurcan et al. 2010 |
| B617 | R-TGTTTTTGGTGGAGCGATG (SEQ ID NO: 8) | Gurcan et al. 2010 |
| B619 | R-GCGATCTGACCTCATTTTTG (SEQ ID NO: 10) | Gurcan et al. 2010 |
| B634 | R-GTGCAGAGGTTGCACTCAAA (SEQ ID NO: 12) | Gurcan et al. 2010 |
| B671 | R-ACCAGCTCTGGGCTTAACAC (SEQ ID NO: 14) | Gurcan et al. 2010 |
| B709 | R-GCGAAATGGAGCTCTTGAAC (SEQ ID NO: 16) | Gurcan et al. 2010 |
| B733 | R-CATCCCCTGTTGGAGTTTTC (SEQ ID NO: 18) | Gurcan et al. 2010 |
| B749 | R-TCGGCTAGGGTTAGGGTTTT (SEQ ID NO: 20) | Gurcan et al. 2010 |
| B767 | R-GCGAAATGGAGCTCTTGAAC (SEQ ID NO: 22) | Gurcan et al. 2010 |
| B774 | R-TGTGTGTGGTCTGTAGGCACT (SEQ ID NO: 24) | Gurcan et al. 2010 |
| B795 | R-TGGGCATCATCCAGGTCTA (SEQ ID NO: 26) | Gurcan et al. 2010 |
| C115 | GTTTCCAGATCTGCCTCCATAAAT (SEQ ID NO: 28) | Bassil et al. 2005b, Gokirmak et al. 2009 |
| KG807 | FAM-CTTACAGATAAATGGCTCAAA (SEQ ID NO: 30) | Gurcan and Mehlenbacher 2010 |
| KG809 | F-GGAAGGTGAGAGAAATCAAGT (SEQ ID NO: 32) | Gurcan and Mehlenbacher 2010 |
| KG811 | F-GAACAACTGAAGACAGCAAAG (SEQ ID NO: 34) | Gurcan and Mehlenbacher 2010 |
| KG827 | GAGGGAGCAAGTCAAAGTTGAGAAGAAA (SEQ ID NO: 36) | Gurcan and Mehlenbacher 2010 |
| KG830 | AAAGCAACTCATAGCTGAAGTCCAATCA (SEQ ID NO: 38) | Gurcan and Mehlenbacher 2010 |
| Soman-G (=856-MS1-13) | R-GCCATCTTTAGAAAGTTCGATACAG (SEQ ID NO: 40) | unpublished |

Primer fluorescent tags are FAM, HEX, and NED.
Ta: annealing temperature (° C.)
N: number of alleles
He: expected heterozygosity
Ho: observed heterozygosity
PIC: polymorphism information content
r: estimated null allele frequency
LG: linkage group
Reference: for development and characterization

TABLE 2

Allele sizes in Wepstee and other hazelnut cultivars at 20 microsatellite loci.

| Locus | Wepster | Tonda Pacifica | OSU 440.005 | Tonda Gentile delle Langhe | Barcelona |
|---|---|---|---|---|---|
| A614 | 135/158 | 135/150 | 125/158 | 125/135 | 125/132 |
| A616 | 152/160 | 150/160 | 152/160 | 150/152 | 144/152 |
| A640 | 368/374 | 368/374 | 355/368 | 355/368 | 355/374 |
| B617 | 293/295 | 293/293 | 293/295 | 285/295 | 285/289 |
| B619 | 166/172 | 166/172 | 166/166 | 150/166 | 158/172 |
| B634 | 228/228 | 228/228 | 228/234 | 228/228 | 228/228 |
| B671 | 239/249 | 229/239 | 249/249 | 239/243 | 225/229 |
| B709 | 229/235 | 229/235 | 223/229 | 229/229 | 227/235 |

TABLE 2-continued

Allele sizes in Wepstee and other hazelnut cultivars at 20 microsatellite loci.

| | | | | | |
|---|---|---|---|---|---|
| B733 | 173/175 | 173/175 | 173/175 | 173/175 | 173/175 |
| B749 | 207/209 | 207/209 | 209/209 | 207/209 | 209/209 |
| B767 | 200/242 | 200/218 | 212/242 | 214/218 | 214/240 |
| B774 | 203/207 | 203/207 | 203/211 | 203/211 | 203/207 |
| B795 | 333/333 | 315/333 | 333/333 | 315/333 | 333/333 |
| C115 | 183/194 | 174/183 | 194/216 | 174/174 | 174/194 |
| KG807 | 252/252 | 228/252 | 252/252 | 238/252 | 238/252 |
| KG809 | 342/342 | 339/342 | 342/348 | 339/342 | 339/339 |
| KG811 | 257/257 | 245/257 | 257/267 | 257/267 | 261/267 |
| KG827 | 270/282 | 270/284 | 272/282 | 268/278 | 282/284 |
| KG830 | 295/305 | 291/295 | 295/305 | 291/295 | 291/295 |
| Soman-G | 196/200 | 196/200 | 196/196 | 196/200 | 196/200 |

| Locus | Vanillin | Dorris | York | Felix | Santiam | Gasaway |
|---|---|---|---|---|---|---|
| A614 | 132/158 | 132/158 | 124/158 | 138/143 | 132/158 | 143/158 |
| A616 | 150/150 | 150/152 | 144/152 | 150/152 | 150/152 | 150/150 |
| A640 | 355/368 | 372/374 | 363/374 | 368/372 | 355/362 | 362/368 |
| B617 | 289/295 | 287/295 | 287/289 | 287/287 | 285/295 | 291/295 |
| B619 | 158/172 | 158/166 | 158/166 | 158/166 | 158/166 | 172/176 |
| B634 | 236/236 | 228/228 | 228/236 | 228/236 | 222/236 | 222/234 |
| B671 | 225/243 | 229/249 | 243/249 | 229/237 | 225/237 | 237/249 |
| B709 | 229/229 | 229/229 | 229/233 | 229/233 | 229/229 | 229/229 |
| B733 | 181/185 | 173/181 | 173/181 | 175/181 | 175/181 | 175/175 |
| B749 | 209/209 | 207/207 | 209/209 | 207/207 | 209/209 | 207/209 |
| B767 | 214/238 | 214/218 | 236/238 | 214/214 | 212/214 | 214/214 |
| B774 | 203/211 | 203/207 | 203/209 | 203/213 | 209/213 | 203/209 |
| B795 | 333/333 | 333/333 | 333/333 | 321/333 | 317/333 | 317/319 |
| C115 | 197/216 | 194/216 | 197/197 | 197/216 | 194/197 | 216/219 |
| KG807 | 230/252 | 242/252 | 242/252 | 238/242 | 242/252 | 242/252 |
| KG809 | 348/348 | 339/348 | 339/348 | 339/348 | 339/342 | 339/348 |
| KG811 | 251/261 | 257/267 | 257/257 | 251/267 | 257/267 | 257/261 |
| KG827 | 268/282 | 272/284 | 268/272 | 272/284 | 272/272 | 272/282 |
| KG830 | 291/295 | 295/297 | 295/295 | 293/303 | 291/295 | 291/305 |
| Soman-G | 196/200 | 196/200 | 196/200 | 196/200 | 196/200 | 196/196 |

References:

Bassil N. V., Botta R., Mehlenbacher S. A. 2005a. Microsatellite markers in hazelnut: Isolation, characterization and cross-species amplification. J. Amer. Soc. Hort. Sci. 130: 543-549.

Bassil N. V., Botta R., Mehlenbacher S. A. 2005b. Additional microsatellite markers of the European hazelnut. Acta Hort. 686:105-110.

Boccacci P., Akkak A., Bassil N. V., Mehlenbacher S. A., Botta R. 2005. Characterization and evaluation of microsatellite loci in European hazelnut (*C. avellana*) and their transferability to other *Corylus* species. Molec. Ecol. Notes 5:934-937.

Boccacci P., Akkak, A. and Botta, R. 2006. DNA typing and genetic relations among European hazelnut (*Corylus avellana* L.) cultivars using microsatellite markers. Genome 49:598-611.

Gökirmak T., Mehlenbacher S. A., Bassil N. V. 2009. Characterization of European hazelnut (*Corylus avellana*) cultivars using SSR markers. Genetic Resources and Crop Evolution 56:147-172.

Gürcan, K., S. A. Mehlenbacher and V. Erdogan. 2010a. Genetic diversity in hazelnut cultivars from Black Sea countries assessed using SSR markers. Plant Breeding (available on-line doi :10. 1111/j. 1439-0523. 2009. 01753. x).

Gürcan, K., S. A. Mehlenbacher, N. V. Bassil, P. Boccacci, A. Akkak and R. Botta. 2010b. New microsatellite markers for *Corylus avellana* from enriched libraries. Tree Genetics and Genomes (available on-line as DOI 10.1007/s11295-010-0269-y).

Gürcan, K. and S. A. Mehlenbacher. 2010. Development of microsatellite marker loci for European hazelnut (*Corylus avellana* L.) from ISSR fragments. Molecular Breeding (available on-line).

SEQUENCE LISTING

```
<160> NUMBER OF SEQ ID NOS: 40

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1

tggcagagct ttgtcagctt                                                20


<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2

gcagtggagg attgctgact                                                20


<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide
```

-continued

<400> SEQUENCE: 3 cactcatacc gcaaactcca 20

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4 atggcttttg cttcgttttg 20

<210> SEQ ID NO 5
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 5 tgcctctgca gttagtcatc aaatgtagg 29

<210> SEQ ID NO 6
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 6 cgccatataa ttggatgctt gttg 24

<210> SEQ ID NO 7
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 7 tccgtgttga gtatggacga 20

<210> SEQ ID NO 8
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 8 tgtttttggt ggagcgatg 19

<210> SEQ ID NO 9
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 9 agtcggctcc ccttttctc 19

<210> SEQ ID NO 10

-continued

<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 10 gcgatctgac ctcatttttg 20

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 11 cctgcatcca ggactcatta 20

<210> SEQ ID NO 12
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 12 gtgcagaggt tgcactcaaa 20

<210> SEQ ID NO 13
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 13 ttgccagtgc atactctgat g 21

<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14 accagctctg ggcttaacac 20

<210> SEQ ID NO 15
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 15 ccaccaactg tttcacacca 20

<210> SEQ ID NO 16
<211> LENGTH: 20
<212> TYPE: DNA
<213> ORGANISM: Artificial Sequence
<220> FEATURE:
<223> OTHER INFORMATION: Synthetic polynucleotide -continued

<400> SEQUENCE: 16 gcgaaatgga gctcttgaac 20

<210> SEQ ID NO 17
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 17 caccctcttc accacctcat 20

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 18 catcccctgt tggagttttc 20

<210> SEQ ID NO 19
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 19 ggctgacaac acagcagaaa 20

<210> SEQ ID NO 20
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 20 tcggctaggg ttagggtttt 20

<210> SEQ ID NO 21
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 21 ccaccaactg tttcacacca 20

<210> SEQ ID NO 22
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 22 gcgaaatgga gctcttgaac 20

<210> SEQ ID NO 23

-continued

<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 23 gttttgcgag ctcattgtca 20

<210> SEQ ID NO 24
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 24 tgtgtgtggt ctgtaggcac t 21

<210> SEQ ID NO 25
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 25 gacccacaaa caataaccta tctc 24

<210> SEQ ID NO 26
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 26 tgggcatcat ccaggtcta 19

<210> SEQ ID NO 27
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 27 attttccgca gataatacag g 21

<210> SEQ ID NO 28
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 28 gtttccagat ctgcctccat ataat 25

<210> SEQ ID NO 29
<211> LENGTH: 18
<212> TYPE: DNA
<213> ORGANISM: Artificial Sequence
<220> FEATURE:
<223> OTHER INFORMATION: Synthetic polynucleotide -continued

<400> SEQUENCE: 29 aagcaagaaa gggatggt 18

<210> SEQ ID NO 30
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 30 cttacagata aatggctcaa a 21

<210> SEQ ID NO 31
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 31 aggcatcagt tcatccaa 18

<210> SEQ ID NO 32
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 32 ggaaggtgag agaaatcaag t 21

<210> SEQ ID NO 33
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 33 aaggcggcac tcgctcac 18

<210> SEQ ID NO 34
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 34 gaacaactga agacagcaaa g 21

<210> SEQ ID NO 35
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 35 agaactccga ctaataatcc taacccttgc 30

<210> SEQ ID NO 36

-continued

<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 36 gagggagcaa gtcaaagttg agaagaaa 28

<210> SEQ ID NO 37
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 37 tggaggaagt tttgaatggt agtagagga 29

<210> SEQ ID NO 38
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 38 aaagcaactc atagctgaag tccaatca 28

<210> SEQ ID NO 39
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 39 tggcgttgca acatattctc 20

<210> SEQ ID NO 40
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 40 gccatcttta gaaagttcga tacag 25

We claim:

1. A new and distinct cultivar of *Corylus* plant named 'Wepster', as illustrated and described.

* * * * *